(12) United States Patent
Lim et al.

(10) Patent No.: US 9,795,479 B2
(45) Date of Patent: Oct. 24, 2017

(54) APPARATUS AND SET FOR FOLDING OR UNFOLDING A MEDICAL IMPLANT COMPRISING A CLAMPING MECHANISM, IMPLANT AND METHOD

(71) Applicant: VENUS MEDTECH (HANGZHOU), INC., Hangzhou (CN)

(72) Inventors: Hou-Sen Lim, Singapore (SG); Wolfgang Götz, Regensburg (DE)

(73) Assignee: VENUS MEDTECH (HANGZHOU), INC., Hangzhou (CN)

(*) Notice: Subject to any disclaimer, the term of this patent is extended or adjusted under 35 U.S.C. 154(b) by 197 days.

(21) Appl. No.: 14/655,714

(22) PCT Filed: Dec. 24, 2013

(86) PCT No.: PCT/EP2013/077973
§ 371 (c)(1),
(2) Date: Jun. 25, 2015

(87) PCT Pub. No.: WO2014/102268
PCT Pub. Date: Jul. 3, 2014

(65) Prior Publication Data
US 2015/0335426 A1    Nov. 26, 2015

(30) Foreign Application Priority Data

Dec. 27, 2012  (EP) .................................... 12008632
May 14, 2013  (EP) .................................... 13002534
Aug. 2, 2013   (EP) .................................... 13003879

(51) Int. Cl.
*A61F 2/95*   (2013.01)
*A61F 2/24*   (2006.01)

(52) U.S. Cl.
CPC .............. *A61F 2/2439* (2013.01); *A61F 2/95* (2013.01); *A61F 2002/9511* (2013.01); *A61F 2002/9522* (2013.01)

(58) Field of Classification Search
CPC .... A61F 2/2427; A61F 2/2439; A61F 2/2466; A61F 2/95; A61F 2002/9505; A61F 2002/9511; A61F 2002/9522
See application file for complete search history.

(56) References Cited

U.S. PATENT DOCUMENTS 4,913,141 A * 4/1990 Hillstead ................... A61F 2/88
                                                    606/194
5,019,085 A * 5/1991 Hillstead ................... A61F 2/88
                                                    606/198
(Continued)

FOREIGN PATENT DOCUMENTS

FR        2946865 A1   12/2010
WO    2005/084595 A1    9/2005
(Continued)

OTHER PUBLICATIONS

PCT/EP2013/077973, International Search Report, dated Mar. 7, 2014.

*Primary Examiner* — Ryan J Severson
(74) *Attorney, Agent, or Firm* — Hamre, Schumann, Mueller & Larson, P.C.

(57) ABSTRACT

The present invention relates to an apparatus (100) for folding or unfolding at least one medical implant (300) by using at least one tension thread (11, 11'), wherein the apparatus (100) includes a shaft (1) including a reception area for receiving the implant (300), a tensioning device for altering a shape of the foldable and/or unfoldable implant (300) by the tension thread (11, 11'), and a clamping mechanism for clamping at least one section of at least one
(Continued)

of the tension threads (11, 11'). The present invention further relates to a set and a method.

21 Claims, 15 Drawing Sheets

(56) References Cited

U.S. PATENT DOCUMENTS

| | | | | |
|---|---|---|---|---|
| 5,387,235 A | * | 2/1995 | Chuter | A61B 17/0469 606/194 |
| 5,405,378 A | * | 4/1995 | Strecker | A61F 2/04 606/194 |
| 5,456,713 A | * | 10/1995 | Chuter | A61B 17/0469 606/194 |
| 5,693,083 A | * | 12/1997 | Baker | A61B 17/11 606/195 |
| 5,693,084 A | * | 12/1997 | Chuter | A61B 17/0469 606/194 |
| 5,755,777 A | * | 5/1998 | Chuter | A61B 17/0469 606/195 |
| 6,346,118 B1 | * | 2/2002 | Baker | A61B 17/11 623/1.12 |
| 6,645,240 B2 | * | 11/2003 | Yee | A61F 2/95 606/192 |
| 7,329,275 B2 | * | 2/2008 | Yee | A61F 2/95 623/1.11 |
| 7,611,528 B2 | * | 11/2009 | Goodson, IV | A61F 2/962 623/1.11 |
| 7,803,177 B2 | * | 9/2010 | Hartley | A61F 2/95 606/108 |
| 7,837,727 B2 | * | 11/2010 | Goetz | A61F 2/2418 623/1.15 |
| 7,947,075 B2 | * | 5/2011 | Goetz | A61F 2/2418 623/1.15 |
| 8,092,510 B2 | * | 1/2012 | Metcalf | A61F 2/95 623/1.12 |
| 9,173,756 B2 | * | 11/2015 | Hopkins | A61F 2/95 |
| 9,278,017 B2 | * | 3/2016 | Rasmussen | A61F 2/95 |
| 9,314,355 B2 | * | 4/2016 | Styrc | A61F 2/95 |
| 9,433,502 B2 | * | 9/2016 | Goetz | A61F 2/2439 |
| 2002/0091439 A1 | * | 7/2002 | Baker | A61B 17/11 623/1.36 |
| 2002/0099432 A1 | * | 7/2002 | Yee | A61F 2/95 623/1.11 |
| 2003/0195607 A1 | * | 10/2003 | Trout, III | A61B 17/064 623/1.13 |
| 2003/0225445 A1 | * | 12/2003 | Derus | A61F 2/95 623/1.11 |
| 2003/0233140 A1 | * | 12/2003 | Hartley | A61F 2/95 623/1.11 |
| 2004/0049256 A1 | * | 3/2004 | Yee | A61F 2/95 623/1.12 |
| 2005/0119722 A1 | * | 6/2005 | Styrc | A61F 2/95 623/1.12 |
| 2007/0100427 A1 | | 5/2007 | Perouse | |
| 2007/0203561 A1 | | 8/2007 | Forster et al. | |
| 2008/0140178 A1 | * | 6/2008 | Rasmussen | A61F 2/95 623/1.11 |
| 2009/0005863 A1 | * | 1/2009 | Goetz | A61F 2/2418 623/2.18 |
| 2009/0099640 A1 | * | 4/2009 | Weng | A61F 2/95 623/1.11 |
| 2011/0040366 A1 | * | 2/2011 | Goetz | A61F 2/2418 623/1.12 |
| 2011/0040374 A1 | * | 2/2011 | Goetz | A61F 2/2418 623/2.11 |
| 2012/0277734 A1 | * | 11/2012 | Goetz | A61F 2/2439 606/1 |
| 2013/0091688 A1 | * | 4/2013 | Goetz | A61F 2/95 29/505 |
| 2013/0103131 A1 | * | 4/2013 | Goetz | A61F 2/2439 623/1.11 |
| 2013/0245752 A1 | * | 9/2013 | Goetz | A61F 2/2439 623/2.11 |
| 2013/0325101 A1 | * | 12/2013 | Goetz | A61F 2/2439 623/1.11 |
| 2015/0335426 A1 | * | 11/2015 | Lim | A61F 2/2439 623/2.11 |

FOREIGN PATENT DOCUMENTS

| | | |
|---|---|---|
| WO | 2011/063972 A1 | 6/2011 |
| WO | 2011/063972 A8 | 7/2011 |
| WO | 2013/021374 A2 | 2/2013 |

* cited by examiner

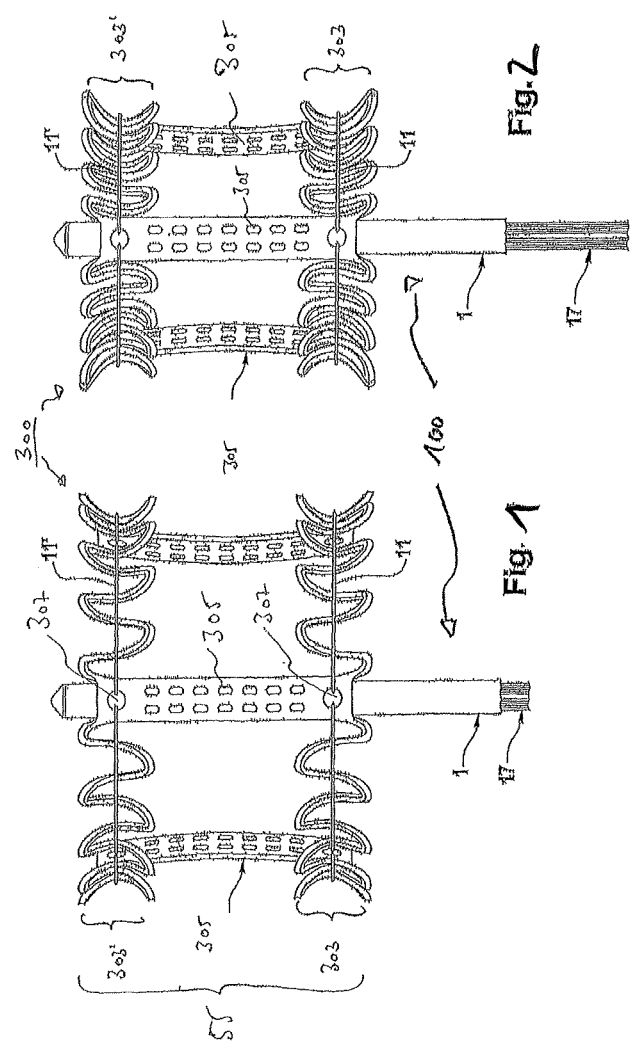

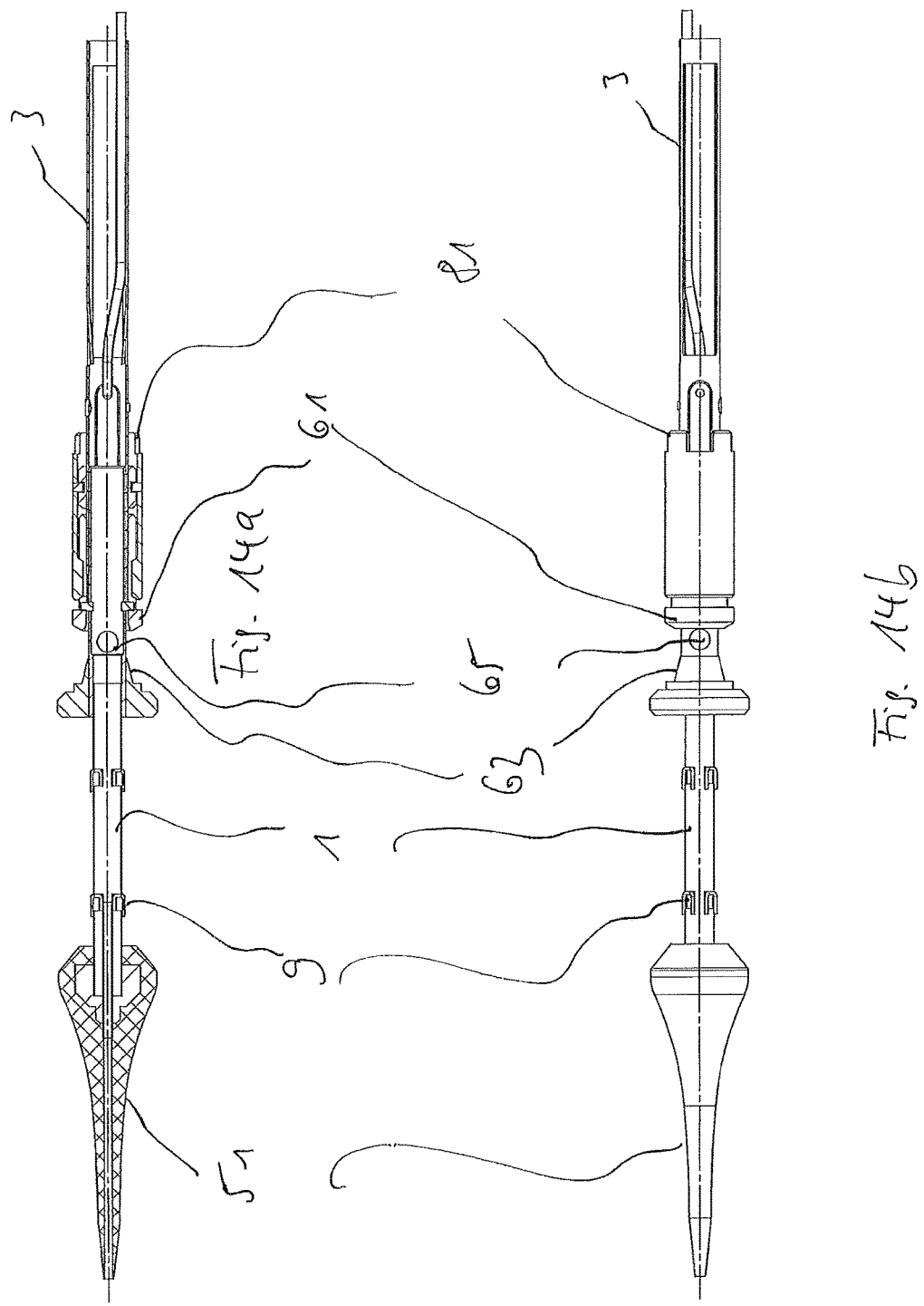

APPARATUS AND SET FOR FOLDING OR UNFOLDING A MEDICAL IMPLANT COMPRISING A CLAMPING MECHANISM, IMPLANT AND METHOD

The present invention relates to an apparatus according to claim 1 for folding or unfolding an implant, to a medical implant (short hereinafter: implant) according to claim 15 and to a set according to claim 16. The present invention further relates to a method according to claim 17.

From practice, implants are known which may be folded or unfolded upon implantation by using one or several threads or filaments wound around the implant. Furthermore, corresponding apparatuses for folding and unfolding are known from practice.

One object of the present invention is to suggest an apparatus for folding or unfolding a foldable and/or unfoldable implant by using a tension thread. Furthermore, the present invention provides a suitable set including such an apparatus, a medical implant as well as a method for folding and/or unfolding an implant.

This object may be solved by a device having the features of claim 1.

According to the present invention, an apparatus for introducing and/or folding and/or unfolding an implant inside and/or outside the body of a patient by using at least one tension thread (referred to as singular or plural below) is suggested. The apparatus according to the present invention includes a shaft having a reception area for receiving the implant.

The apparatus further includes at least one tensioning device for altering or amending a shape of the foldable and/or unfoldable implant by the tension thread or by at least one first string connected to the tension threads.

Additionally, the apparatus includes a clamping mechanism, a clamping device or a clamping section (hereinafter: clamping mechanism) for clamping at least one section (for example a free end) of at least one of the tension threads.

Also, the object of the present invention is solved by a medical implant having the features of claim 15. The medical implant comprises a set of tension threads for folding or unfolding the medical implant or is connected or provided herewith, the set being designed as set forth herein.

Further, the object of the present invention is solved by a set of tension threads for folding or unfolding at least one medical implant having the features of claim 16. The set comprises at least one first string, at least a first tension thread and at least a second tension thread. The first string comprises at least a first guiding element for guiding through the first tension thread and a second guiding element for guiding through the second tension thread. Both the first tension thread and the second tension thread are attached to the first string.

Furthermore, the object of the present invention is solved by the method according to claim 17. The method according to the present invention comprises providing an apparatus according to the present invention or a set according to the present invention. It also comprises clamping at least one section of at least one tension thread by a clamping mechanism.

In the following, the use of the expression "may be" or "may have", and so on, is to be understood synonymously with "in exemplary embodiments is" or "in exemplary embodiments has", respectively, and so on, and is intended to illustrate exemplary embodiments according to the present invention.

Whenever numerical values are mentioned herein such as "one", "two" and the like, they have to be understood as values representing the lower threshold of numerical ranges. A long as this does not result in a contradiction in the eyes of the skilled one, numerical values, such as "one" shall be understood as comprising also "at least one". This interpretation or understanding is as well encompassed by the present invention as the understanding according to which a numerical value such as "one" may be understood as "exactly one" whenever this appears technically possible to the skilled person. Both understandings are covered by the present invention. This applies to any numerical value stated herein.

Exemplary embodiments according to the present invention are each also subject of dependent claims.

Exemplary embodiments according to the present invention may comprise one or more of the features named hereafter in any arbitrary combination.

In some exemplary embodiments according to the present invention, altering the shape of the implant means reducing or increasing a diameter, particularly an external diameter, of the implant. Such an alteration may or may not involve an alteration of the implant's length or any other kind of alteration.

In certain exemplary embodiments according to the present invention, folding the implant means reducing the diameter of the implant. Folding also covers "re-folding" of an once expanded implant.

In some exemplary embodiments according to the present invention, unfolding should be understood as increasing the diameter of the implant, or as expanding.

In certain exemplary embodiments according to the present invention, the diameter of the implant is arranged in the reception area in a plane perpendicular to a main flow direction of the implant in case fluids flow through the implant after its implantation.

In some exemplary embodiments of the apparatus according to the present invention, the at least one tension thread is a thread. The thread may be a surgical suture thread or similar to it. The thread may have the shape of a rope, a filament or a cord. The thread may be designed as a chain having a plurality of engaging chain links.

In the following, the term thread or tension thread may also define a plurality of threads or tension threads whenever a person skilled in the art recognizes the exchangeability of the terms.

In certain exemplary embodiments according to the present invention, the shaft of the apparatus is rigid. In some exemplary embodiments according to the present invention, the shaft of the apparatus is flexible in one or more directions (i.e., in a longitudinal direction or in a direction of the width of the shaft, respectively, in both directions or in other directions). In certain exemplary embodiments, the shaft is elongatable. In particular exemplary embodiments according to the present invention, the shaft is stiff.

In certain exemplary embodiments according to the present invention, the implant is permeable for fluids in its implanted state in its longitudinal direction. "Permeable" means that the fluid may flow through the implant, for example, through an inner lumen thereof.

In some exemplary embodiments of the apparatus according to the present invention, the implant is—at least temporarily—mounted or loosely arranged on or at the reception area of the apparatus at the moment of unfolding or folding. In some of these embodiments, the implant is arranged on or at the reception area or is interconnected with the reception area only by the tension threads.

In certain exemplary embodiments of the apparatus according to the present invention, the tensioning device includes at least one pulling device. The pulling device is arranged and/or provided in such a way that it may indirectly or directly apply a tension on the implant for altering the shape of the implant by the tension thread if the pulling device is pulled by an operator (e. g., by the surgeon).

Alternatively or additionally, in some exemplary embodiments of the apparatus according to the present invention, the pulling device is arranged and/or provided in such a way that it may reduce a tension applied on the implant by the tension thread if the pulling device is pulled by an operator (e. g., by the surgeon).

In certain exemplary embodiments of the apparatus according to the present invention, the pulling device is arranged and/or provided such that it may interact with the tension thread in order to transfer force or tension.

In some exemplary embodiment of the apparatus according to the present invention, the pulling device and the tension thread are intricate with each other.

In certain exemplary embodiments according to the present invention, the term "intricate" is used to indicate that the tension thread is movable in at least one direction or in two directions relative to the pulling device.

According to some exemplary embodiments of the present invention, the term "movable" is to be understood as "slidable".

According to certain exemplary embodiments of the present invention, the term "intricate" means that the tension thread is movably arranged relative to the pulling device like a first link of a chain is movably arranged relative to an adjacent second link of this chain to which the first link is usually connected in a chain.

In some exemplary embodiments of the present invention, the term "intricate" shall indicate that the tension thread is simply crossed once with or wrapped around the pulling device or sections thereof.

In certain exemplary embodiments of the present invention, the transfer (or the transmittal, respectively) of force or tension between the pulling device and the tension thread is achieved by a non-form closure connection.

In some exemplary embodiments according to the present invention, the transfer of force or tension between the pulling device and the tension thread is achieved by a frictional connection.

In certain exemplary embodiments of the apparatus according to the present invention, the pulling device is embodied as at least one pulling thread or wire or consists of at least one pulling thread or wire.

In some exemplary embodiment of the apparatus according to the present invention, the tension thread and/or the pulling thread includes or constitutes at least one bundle or a plurality of threads or thread elements or consists thereof.

In certain exemplary embodiments according to the present invention, "clamp" or "clamping" means to fasten the section of the thread within or by the clamping mechanism. It may be understood as to fasten the thread to another part of the apparatus such as the first or second clamping section. The term may be understood as to maintain the section of the thread within or by the clamping mechanism in a manner such that the clamped section of the thread cannot be withdrawn from the clamping mechanism by the tension device under normal use conditions unless the releasing device has been operated. The term may be understood so as press two parts towards each other strongly enough so as to keep an object (here: the section of the thread) arranged between the two parts in place. The term may be also understood as to press the section of the thread against one first clamping section by a second clamping section, wherein at least one of the clamping sections is not movable with regards to the shaft or the entire apparatus.

In some exemplary embodiments according to the present invention, the term "clamping mechanism" relates to a part of the apparatus, or a set of parts thereof that work together in order to clamp the section of the thread in a releasable manner. The releasing device may be arranged to be operated by the surgeon.

In certain exemplary embodiments according to the present invention, the first and the second clamping section may together be understood as a clamp for the thread when clamping the section of the thread between them.

In some exemplary embodiments according to the present invention, the clamping mechanism consists of the first and the second clamping section. In certain exemplary embodiments according to the present invention, the clamping mechanism comprises the first and the second clamping section.

In certain exemplary embodiments according to the present invention the first clamping section and the second clamping section of the apparatus are arranged such that they are inclined to the longitudinal axis of the apparatus, its shaft, and/or the reception or retaining area for receiving the implant.

In some exemplary embodiments according to the present invention, the "releasing device" for releasing the clamp, the clamping mechanism or the clamping of the section of the thread is to be understood as a device for removing restrictions acting on the section of the thread, for removing the section of the thread from at least one of the first or second clamping section, or vice versa, for removing at least one of the first or second clamping section from a fixed position, allowing the section of the thread to move or to be withdrawn, e. g. by the pulling device or by the tensioning device.

In certain exemplary embodiments according to the present invention, the clamping mechanism does not form part of the tensioning device.

In some exemplary embodiments according to the present invention, a first end of the thread is clamped by the clamping mechanism, whereas another part, in particular a second end opposite to the first end of the thread is interconnected with the tensioning device.

In certain exemplary embodiments according to the present invention, the apparatus comprises a releasing device for releasing the clamped section of the tension thread from the implant by releasing the clamping mechanism.

In some exemplary embodiment of the apparatus according to the present invention the clamping mechanism is adapted for clamping the at least one section of at least one of the tension threads between a first clamping section and a second clamping section of the apparatus. Alternatively, the clamping mechanism consists of such first and second clamping sections.

In certain exemplary embodiments according to the present invention, the first clamping section and the second clamping section of the apparatus are arranged such that they may slide relatively to each other (for example, mainly or exclusively in a direction parallel to the main extent or the longitudinal direction of the apparatus).

In some exemplary embodiments according to the present invention, the second clamping section of the apparatus is arranged in an inner space of the first clamping section of the apparatus.

In certain exemplary embodiments according to the present invention, an interior of the shaft is permeable or may be passed in at least sections thereof in the longitudinal direction of the shaft. The shaft has a wall, and the shaft includes at least one shaft aperture through which tension threads for folding and/or unfolding the implant may enter and/or exit the inner lumen of the shaft.

In particular exemplary embodiments according to the present invention, neither the first nor the second clamping section is arranged on or at the implant.

In some exemplary embodiments according to the present invention, the implant is a stent or a cardiac valve assembly.

In particular exemplary embodiments according to the present invention, the apparatus comprises at least one implant connected with tension threads or with a set of tension threads for folding or unfolding at least one medical implant. The combination of an apparatus according to the present invention and at least one implant connected thereto by tension threads or a set of tension threads for folding or unfolding the medical implant may also be called a "set" (albeit different from the set of tension threads according to the present invention, of course).

In some exemplary embodiments according to the present invention, the set of tension threads comprises at least one first string, at least a first tension thread and at least a second tension thread. The first string comprises at least a first guiding element for guiding through the first tension thread and a second guiding element for guiding through the second tension thread. Both the first tension thread and the second tension thread are attached with the first string.

In certain embodiments according to the present invention both the first tension thread and the second tension thread are attached with the first string such that they are fixed to the first string and/or such that the ends or portions of the threads by which they are fixed to the first string cannot move relatively to the first or second guiding element. For example, the first tension thread and the second tension thread may both be knotted to or integral with the first string. In embodiments with more than two tension threads, more than two tension threads are fixed to the first string.

In some exemplary embodiments according to the present invention, at least one of the first guiding element and the second guiding element are rings. In certain embodiments, the first tension thread and the second tension thread may slide through the first guiding element and the second guiding element forth and back.

In certain embodiments according to the present invention the first string is connected to a multitude of tension threads, for example to—at least or exactly—six tension threads of which three are guided through the first guiding element, wherein three of them are guided through the second guiding element.

In certain embodiments according to the invention, neither of the first tension thread nor the second tension thread is directly connected to a tensioning device of a catheter for altering a shape of the foldable and/or unfoldable implant. Rather, they are in direct contact with the first string. It is via the first string that they are in indirect contact with the tensioning device.

In certain embodiments according to the present invention at least the first tension thread is connected to the first string, preferably at a first end section of the first string. Likewise, the second tension thread is connected to the first string, preferably at a second end section of the first string.

In some embodiments according to the present invention the first end section and the second end section are opposed ends of the first string.

In certain embodiments according to the present invention the first tension thread is connected with or fixed at its first end to the first string, and wherein at least the second tension thread is connected with or fixed at its first end to the first string.

In certain exemplary embodiments according to the present invention, the method encompasses releasing the clamped section of the tension thread from the implant by releasing the clamping mechanism. In some of these embodiments the tension thread may then be withdrawn from the implant, e. g. by the tensioning device or the surgeon.

In certain exemplary embodiments according to the present invention, the releasing device it not a wire or a thread (or a multitude thereof, respectively).

In some exemplary embodiments according to the present invention, the releasing device is not embodied as a lock wire or lock thread that is withdrawn from the apparatus so as to allow the tension threads to be removed from the apparatus after final placement of the implant.

In certain exemplary embodiments according to the present invention, the releasing device does not comprise hooks and/or does not comprise rings for guiding or limiting tension strings or threads.

In some exemplary embodiments according to the present invention, the releasing device is embodied and/or intended to stay with the apparatus even after termination of the implantation of the implant.

In certain exemplary embodiments according to the present invention, the releasing device may not be separated from the apparatus except for cleaning or the like.

In some exemplary embodiments according to the present invention, the releasing device is embodied such that it is intended or configured to be used, according to the present invention, only within the patient's body.

In some exemplary embodiments according to the present invention, at least one of the first or the second clamping device is or includes at least one sleeve. The sleeve may preferably be made tube-like (that is, it may have a hollow inside), like a hollow cylinder, like a ring or the like. The sleeve may be manufactured symmetrically or asymmetrically, both relative to its opening direction and in another direction, particularly in a direction or plane perpendicular to the opening direction or the fluid passage direction, as well.

In certain exemplary embodiments of the apparatus according to the present invention, the sleeve aperture is designed as a passage opening or a through opening. It may thus be as thick as the wall of the sleeve is in a radial direction of the apparatus.

In some exemplary embodiments of the apparatus according to the present invention, the releasing device is no cutting device for cutting through the tension thread, and it does not comprise one.

In certain exemplary embodiments according to the present invention, the shaft of the apparatus is permeable or has a passage for fluids in its interior in at least some sections of its longitudinal direction. The shaft has a wall.

In some exemplary embodiments according to the present invention, the shaft includes at least one shaft aperture.

The at least one shaft aperture may preferably be arranged on a lateral area or on the circumference of the shaft rather than on the front side thereof.

In some exemplary embodiment of the present invention, the shaft of the apparatus includes a plurality of shaft apertures being uniformly or non-uniformly distributed along one or more circumferences and/or along the longitudinal extension of the shaft.

In certain exemplary embodiments according to the present invention tension threads for folding and/or unfolding the implant may enter and/or leave the apparatus through the shaft aperture.

In some exemplary embodiments according to the present invention, the releasing device is identical to the clamping mechanisms or comprises part of it. In these embodiments, there is one device that may both clamp and subsequently also release the thread when being operated in a "reverse manner".

In certain exemplary embodiments according to the present invention, the first or the second clamping section is preferably arranged in a shiftable manner.

In some exemplary embodiments according to the present invention, the first clamping section surrounds or embraces the shaft in such a way that the shaft is located inside the first clamping section and the first clamping section. Alternatively, the first clamping section may be located inside of the shaft such that the shaft is surrounding the sleeve.

In certain exemplary embodiments according to the present invention, the apparatus includes a releasing device which is arranged for exerting tension on the first or second clamping device in at least one state of use.

In some exemplary embodiments according to the present invention, the releasing device exerts a tension on the first or second clamping device substantially or exclusively in a longitudinal direction of the shaft In certain exemplary embodiments of the apparatus according to the present invention, the releasing device is arranged for pushing or for pulling the first or second clamping device in order to release the clamped section of the thread. It may be embodied as a pulling device as, e.g., a thread or the like. In other exemplary embodiments, said device is embodied as a pushing or twisting device.

In some exemplary embodiments according to the present invention, the releasing device enables a transition from the clamping position into the release or non-clamping position.

In certain exemplary embodiments of the apparatus according to the present invention, said releasing device is arranged such that it enables a transition from the clamping position into the release or non-clamping position independently from an operation of the tensioning device.

In some exemplary embodiments according to the present invention, the apparatus is arranged for folding and/or unfolding an implant having the shape of a stent or a cardiac valve assembly.

In certain exemplary embodiments of the apparatus according to the present invention, the implant is a foldable and/or unfoldable implant.

In some exemplary embodiments according to the present invention, the apparatus is a catheter or a tip of a catheter that is provided to be interconnected with a catheter.

In certain exemplary embodiments according to the present invention, the method comprises altering the tension that is exerted on an implant by using at least one tension thread. The tension is preferably controlled by altering a length of the pulling device by which it extends out of the interior of the shaft or sections thereof.

In some exemplary embodiments according to the present invention, at least one of the apparatus, the implant and the set comprises exclusively, i.e. only, (one or more) materials that are MRI (short for: magnetic resonance imaging) compatible. In certain exemplary embodiments according to the present invention, at least one of the apparatus, the implant and the set comprises exclusively (one or more) materials that are not magnetic, ferromagnetic, or both. In some exemplary embodiments according to the present invention, at least one of the apparatus, the implant and the set does not comprise metal or any metal alloy.

In particular exemplary embodiments according to the present invention, the method comprises monitoring or controlling the position of the apparatus or the implant, or both, by means of magnetic resonance imaging (MRI) during or after implementation, advancing or delivering of the implant.

In certain exemplary embodiments according to the present invention, all instruments used for implanting or advancing the implant are MRI compatible.

In some embodiments according to the present invention, the apparatus comprises a detachable tip. In certain embodiments according to the present invention, the tip (and only the tip) comprises the first and the second clamping section.

In particular embodiments according to the present invention, the first clamping section is connected to a first connecting device of the tip or the shaft of the apparatus by a thread such that the first clamping section can be moved along the shaft of the tip by rotating the first connecting device whereas the first clamping section itself is not rotated.

In some embodiments according to the present invention, the tip of the apparatus comprises a rotational clamping mechanism such that the first clamping section can be moved to or away from the second clamping section by rotating the first connecting device whereas the first clamping section itself is not rotated.

In particular embodiments according to the present invention, the first connecting device may have an crown-shaped section, it may comprise a gear pattern, it may have teeth or any other engagement device, due to space constraints preferably at its front surface (not on its sided surface), configured to be engageable with a second, rotably arranged connecting device of the apparatus in a manner such that via rotating the second connecting device the first connecting device may be rotated.

In certain embodiments according to the present invention, the clamping surface of at least one of the first and second clamping sections is inclined against a longitudinal axis of the apparatus or the tip thereof by between 10 and 30 degree, preferably between 10 and 20 degree, most preferably about 15 degree.

In some embodiments according the present invention, the entire rotational clamping mechanism, including or consisting of at least the first and the second clamping section and the first connecting device, is provided on or at the side of the tip.

In certain embodiments according to the present invention, the first clamping section has a clamping surface, is movably arranged, comprises a thread (preferably arranged on an inner surface thereof), has a slot or groove (which preferably is straight) into which a protrusion such as a pin is inserted, whereas the protrusion is fixed to the tip, but cannot be rotated.

In some embodiments according to the present invention, the the first clamping section has a clamping surface, is movably arranged, comprises a thread (preferably arranged on an outer surface thereof), has a slot or groove (which preferably is straight) into which a protrusion such as a pin is inserted, whereas the protrusion is fixed to the tip, but cannot be rotated.

Some or all advantages achievable by the apparatus according to the present invention may in certain exemplary embodiments of the present invention also be achieved by the set, the implant and by the method according to the present invention.

What is said in here with regard to one tension thread holds also true for a multitude of tension threads whenever this does stand in contrast to the general idea of the present invention.

Some or all exemplary embodiments according to the present invention may provide for one, several or all of the advantages named above and/or hereafter.

Among the advantages achievable according to the present invention is the opportunity of releasing threads from the implant by the releasing device that is arranged for ceasing the clamping of the thread(s).

Further, clamping the threads used for folding or unfolding the implant allows for a safe temporary connection between the apparatus with the threads. At the same time, since the clamping mechanism may be released after implantation, in some exemplary embodiments the present invention allows for an easy removal of the threads from the implant just by releasing or terminating the clamping effect and by pulling the thread out of the apparatus. In particular, for removing the threads from the implant or from the apparatus, no thread has to be untied, unknot, undone or even cut. Hence, at least one end of the tensioning threads does not have to be interconnected to or released from e. g. the implant. This does not only safe time and effort but also contributes to a safe handling of the implant upon implantation. Also, providing a reliable clamping mechanism is less demanding regards observing tolerances in the production process of the apparatus according to the present invention.

Providing a groove, a sliding block guiding, a slotted guide, or the like that avoids twisting or rotation of the first clamping device with regard to the second device or vice versa contributes to releasing the clamped section of the thread once the releasing device has been operated. In contrast, twisting or rotating might incur an accidental clamping of the thread between part of the apparatus other than the first and second clamping sections.

Providing at least one of the apparatus, the implant and the set to be MRI compatible allows advantageously for controlling the location and orientation of the apparatus or the implant, or both, by MRI upon use of the apparatus or implantation of the implant. No heat, sparks or artefacts are generated during MRI because of the materials chosen for the apparatus or the implant.

Among the advantages achievable according to the present invention is the opportunity of independently actuating tension threads. This is due to the self balancing design provided in which the pulling thread is entangled with the first string or wound around without being fixed to it. This way, the first string may move forth and back within the loop of the pulling thread. Thus, it is possible to specifically fold and/or unfold implants having a first and a second tension thread, or a plurality of tension threads, which act on different parts or sections of the implant upon folding the latter. Parts or sections of the implant can thus be folded or unfolded though other parts or sections of the implant have already been completely folded or unfolded. This can i.a. be reasonable when an unfolded implant and the implantation site do not completely match in their dimensions, or if the implant does, e.g., not have a uniform shape over its entire length. For more details regarding the idea of an self-balancing design it is referred to WO 2011063972 A8. See, in particular, FIGS. 2 and 2A thereof. The entire respective content of WO 2011063972 A8 is incorporated herewith by reference.

In the following, examples of the present invention will be described with reference to the accompanying figures wherein similar or identical assemblies or elements are denoted by same reference numbers.

FIG. 1 shows schematically simplified and in part section an apparatus according to the present invention with an expanded implant according to a first exemplary embodiment of the present invention;

FIG. 2 shows the apparatus of FIG. 1 with the implant in a further (partly) folded condition;

Figure 14C:
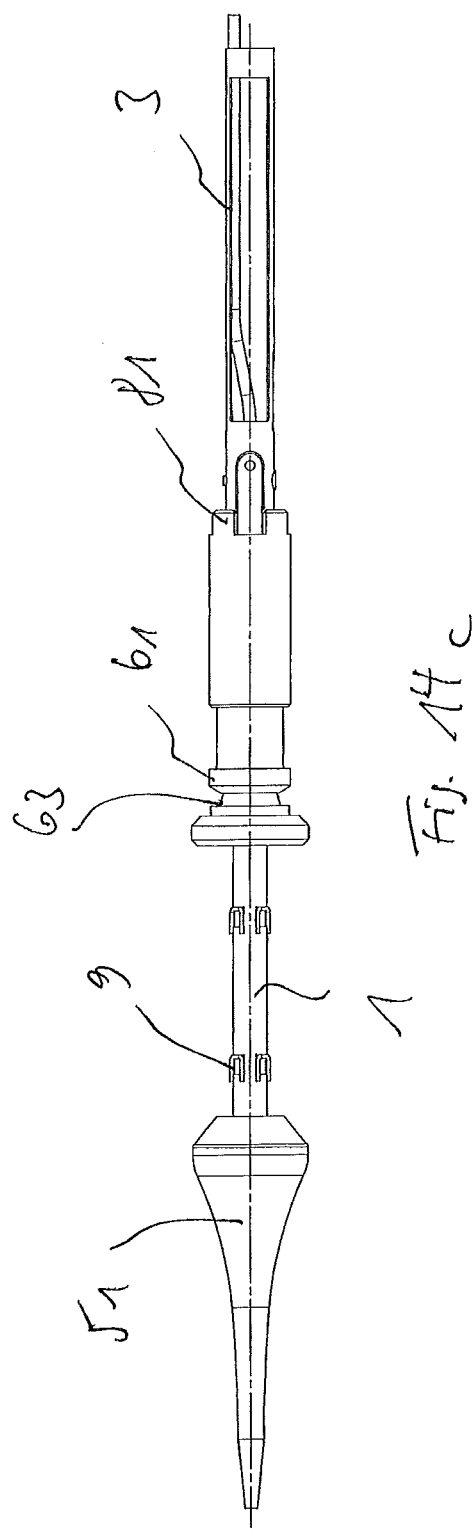
Figure 15A:
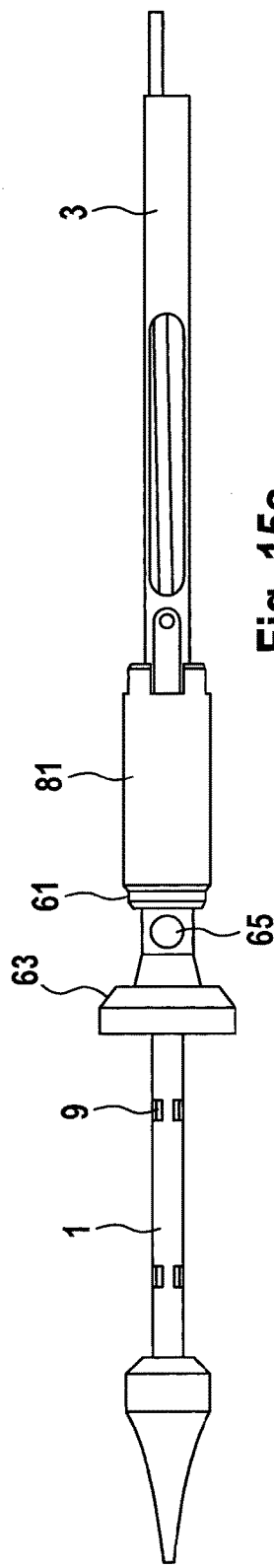
Figure 15B:
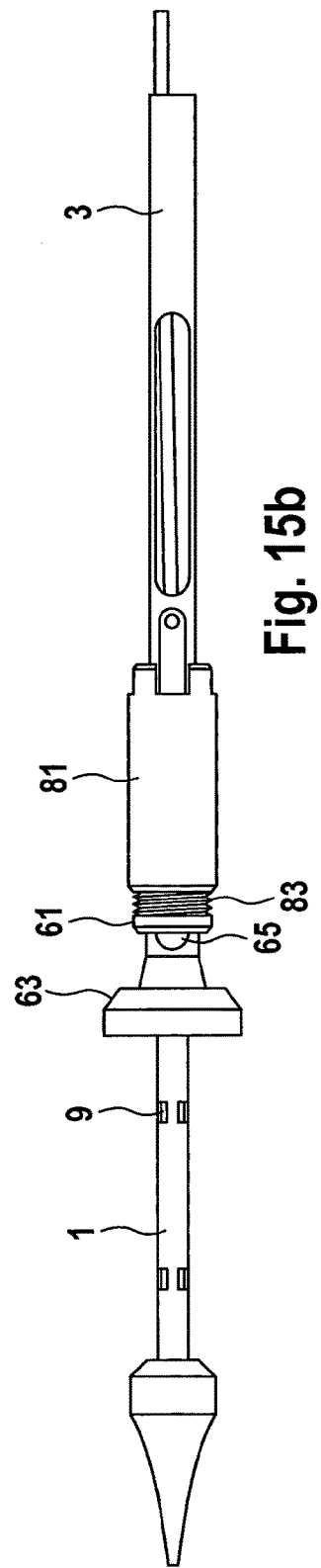
Figure 15C:
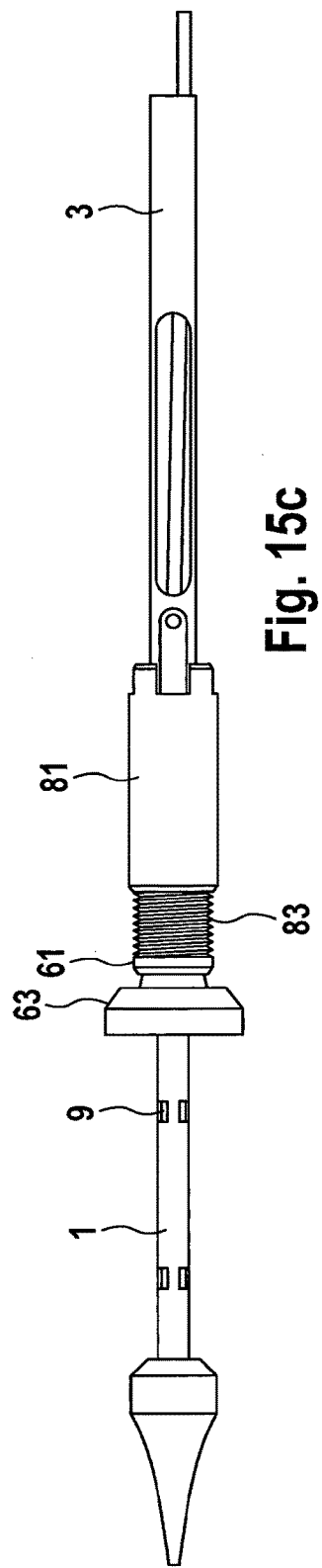

FIG. 14*a* shows a longitudinally cut tip of the apparatus according to the present invention in yet another embodiment, in an unclamping state revealing the first and the second clamping sections of that embodiment;

FIG. 14*b* shows the tip of the apparatus of FIG. 14*b*, not cut;

FIG. 14*c* shows the tip of the apparatus of FIGS. 14*a* and 14*b* in a clamping state;

FIG. 15*a* shows the tip shown in FIGS. 14*a-c* in a unclamped state;

FIG. 15*b* shows the tip shown in FIG. 15*a* in another unclamped state; and FIG. 15*c* shows the tip shown in FIGS. 15*a-b* in a clamped state.

FIG. 1 shows schematically simplified and in part section an apparatus 100 according to the present invention with an expanded implant 300 according to a first exemplary embodiment of the present invention (the combination of apparatus 100 and implant 300 also being referred to as "set" herein).

A first tension thread 11 and a second tension thread 11' are arranged around the implant 300. As can be seen from FIG. 1, the implant 300 comprises a first guiding structure 303 for guiding the first tension thread 11 and a second guiding structure 303' for guiding the second tension thread 11'.

In the exemplary embodiment of FIG. 1, the first guiding structure 303 and the second guiding structure 303' are designed as rings or channel-like ring structures. These structures are optionally radially open but medially closed as it is exemplarily also shown in FIG. 1.

Also by way of example, two, three or more posts 305 are arranged between the first guiding structure 303 and the second guiding structure 303'. The posts 305 each comprises one, two or more openings 307 for letting pass the first or second tension threads 11, 11' from an inside of the implant 300 to on outside thereof.

The posts 305 may be configured to keep the distance between the first guiding structure 303 and the second guiding structure 303'.

In the example of FIG. 1, the threads 11 and 11' are provided for holding the implant 300 with regards to the apparatus 100. In any case, the diameter of the implant 300 or its folding state may be altered by varying the tension of the threads 11 and 11' as will be explained in more detail below.

Figure 3:
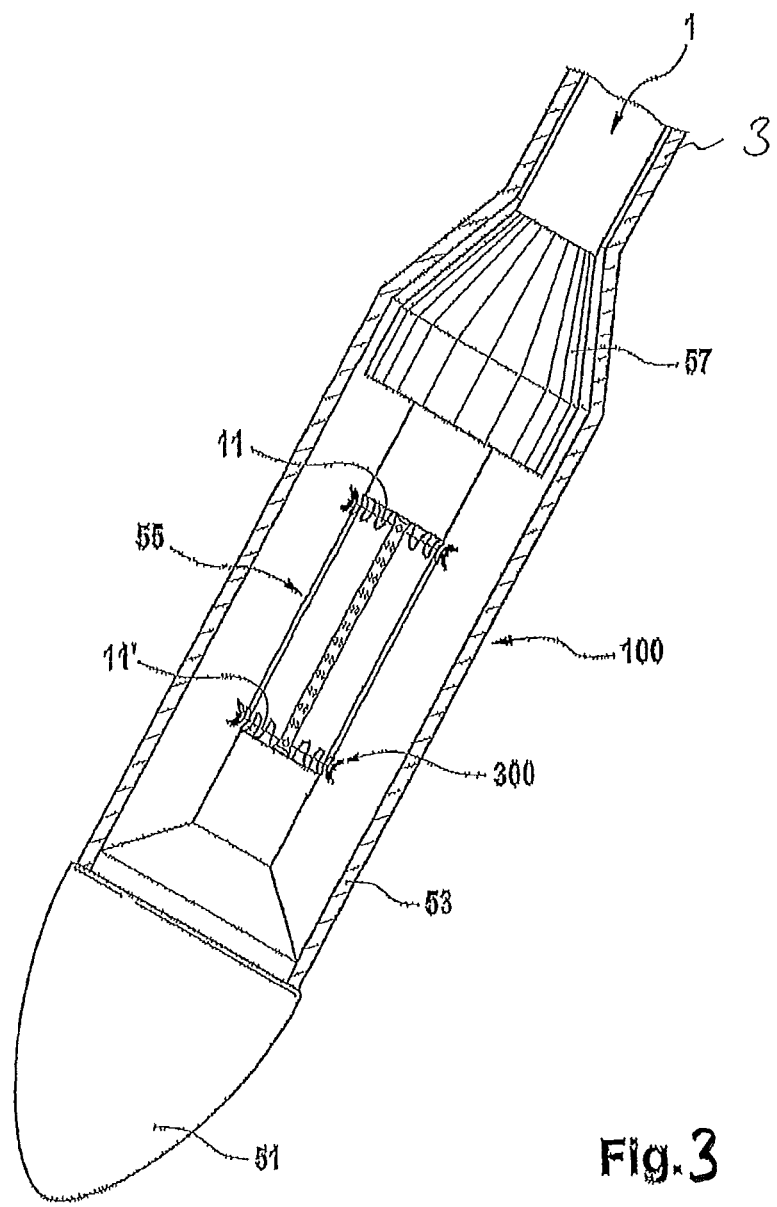
FIG. 3 shows the tip of an apparatus according to the present invention shown in a closed condition prior to implantation.
Figure 13:
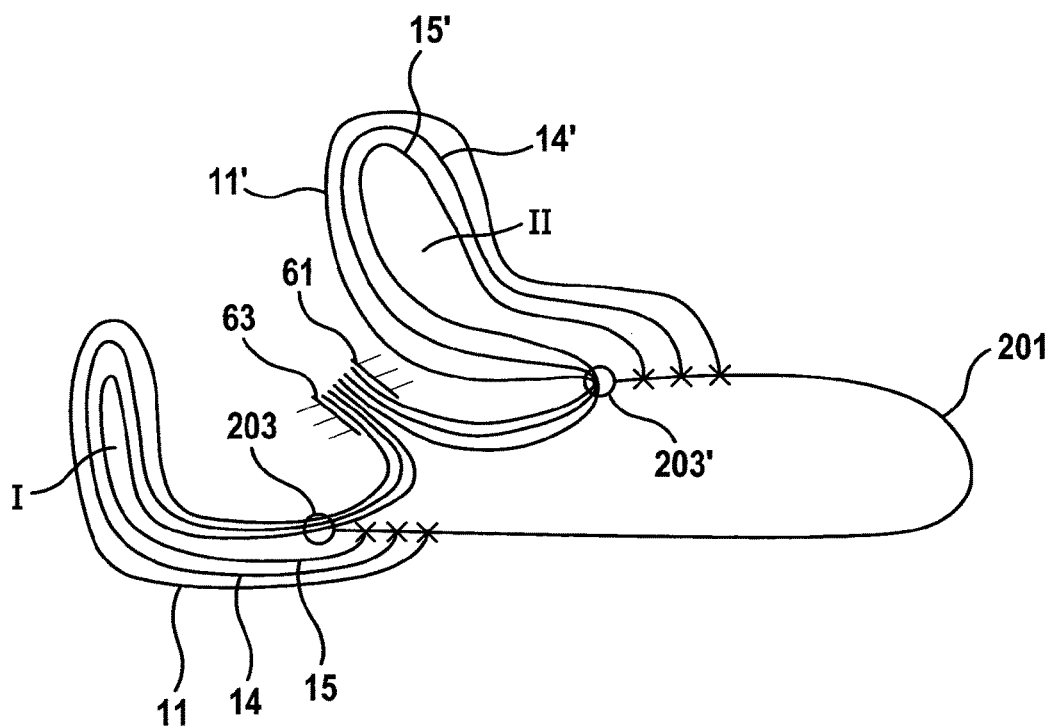
FIG. 13 shows another set according to the present invention in a second embodiment thereof.

The apparatus 100 has a shaft 1 having a lumen covered by a wall (depicted with reference numeral "3" in, e.g., FIGS. 3 and 13). In the lower area of FIG. 1, the wall of shaft 1 is longitudinally cut. Pulling threads 17 arranged within the lumen of the shaft 1 extend therefrom.

The pulling threads 17 are integral with or interconnected to threads 11 and 11' which are guided along the circumference of implant 300 at different levels—by the first and the second guiding structure 303 and 303'—thereof such that pulling or releasing the pulling threads 17 makes the threads 11 and 11' to exert more or less force on the implant 300 as it is also described in the patent application published under WO 2011/063972 A1 This way, operating the pulling threads 17 may provide for a change in one or more cross-section dimensions of the implant 300. The respective disclosure of WO 2011/063972 A1 is incorporated into the present specification by reference.

The threads 11 and 11' enter into the lumen of shaft 1 by apertures 9 not shown in FIG. 1 (but shown in FIG. 5) and they exit shaft 1 from such apertures again.

The expansion of implant 300 may benefit in the present exemplary embodiment from the internal stress or from shape-memory capacities of implant 300. The implant 300 may be manufactured from Nitinol or comprise such material. In order to expand the implant 300, the pulling threads 17 need, however, to be sufficiently released. For folding the implant 300 again, the pulling threads 17 are tightened again.

FIG. 2 shows the apparatus 100 of FIG. 1. The implant 300 is in a partly folded condition (also referred to herein as "folded" or "refolded"). Since folding of the implant 300 has to be achieved by pulling the pulling threads 17, in FIG. 2 the pulling threads 17 protrude further out of shaft 1 than in FIG. 1.

In FIG. 1 (and likewise in FIG. 2), apparatus 100 is shown with only one upper ("second") thread 11' and one lower ("first") thread 11. This reduction (simplification) is used for improved clarity. It is therefore clear that any arbitrary number of upper and lower threads 11 and 11' may be provided ("upper" and "lower" relate to the upright position of the implant shown in FIG. 2). A corresponding number of apertures 9 may be provided.

FIG. 3 shows an apparatus 100 according to the present invention with an implant 300 attached at or within an apparatus 100 according to the present invention.

FIG. 3 shows in part section a tip 51 of an apparatus 100 according to the present invention in a closed condition prior to implantation.

Shown in part section is an outer protective sleeve 53 which gives protection to a retaining area 55 for the implant 300. In the example of FIG. 3, the implant 300 is a stent which is arranged between the tip 51 and a collar 57. The collar 57 may advantageously guide the sleeve over the implant 300 which may be, e. g., a crimped stent, as in the example of FIG. 3.

The implant 300 is held by the threads 11 and 11' in a restrained or folded state in which it is not expanded.

Figure 4:
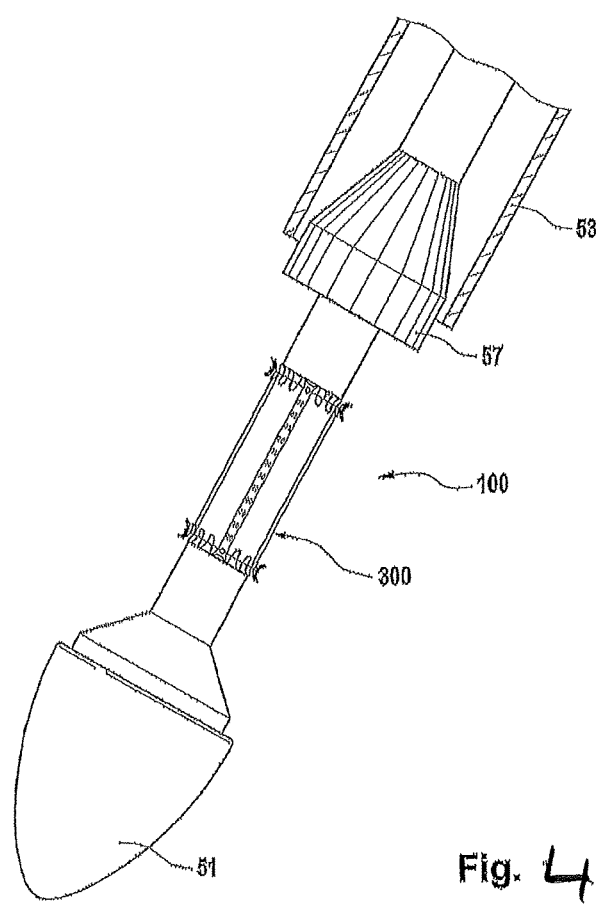
FIG. 4 shows the tip of the apparatus according to the present invention as in FIG. 3 prior to implantation with partially withdrawn outer sleeve.

FIG. 4 shows the tip 51 of FIG. 3 prior to implantation. The outer protective sleeve 53 is partly withdrawn. By withdrawing the outer protective sleeve 53, which is only provided by way of example, the implant 300 is ready for implantation. The restrained state is still maintained, substantially or fully by the tension of the circumferentially wound threads 11 and 11'.

Figure 5:
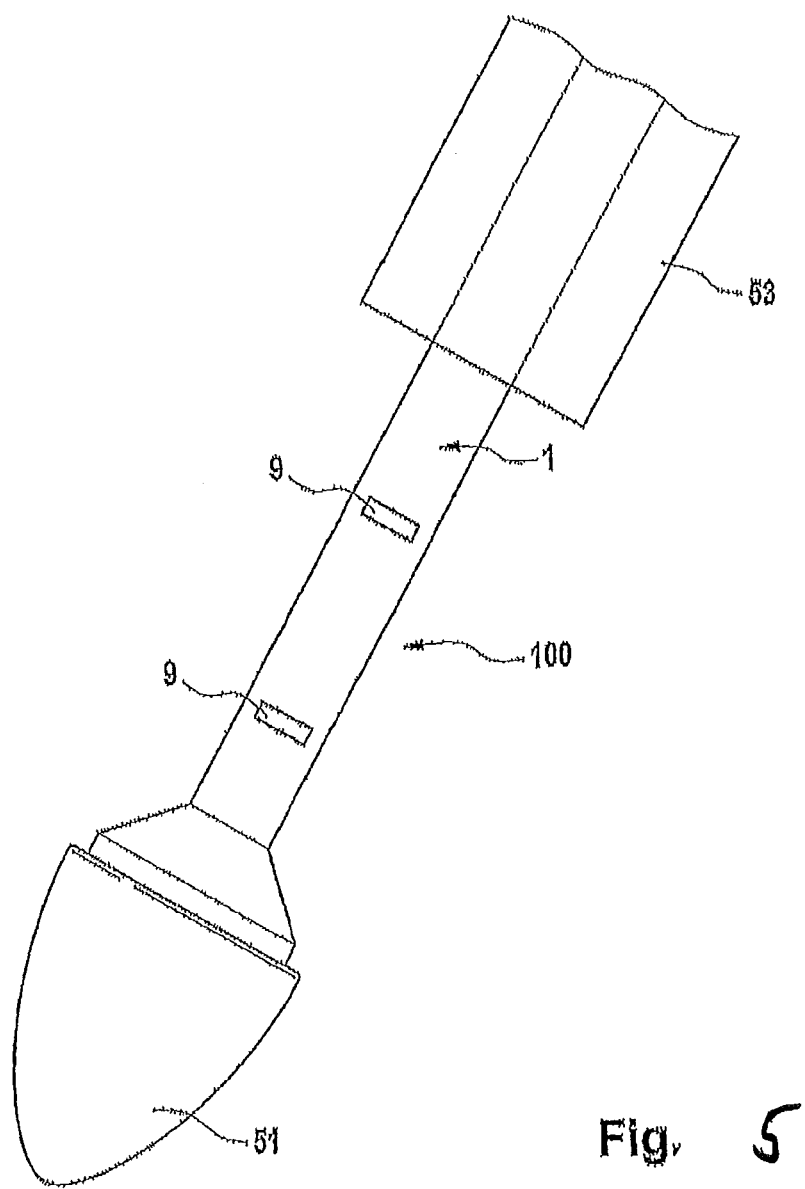
FIG. 5 shows the tip of an apparatus according to the present invention as in FIG. 4 without implant.
Figure 6:
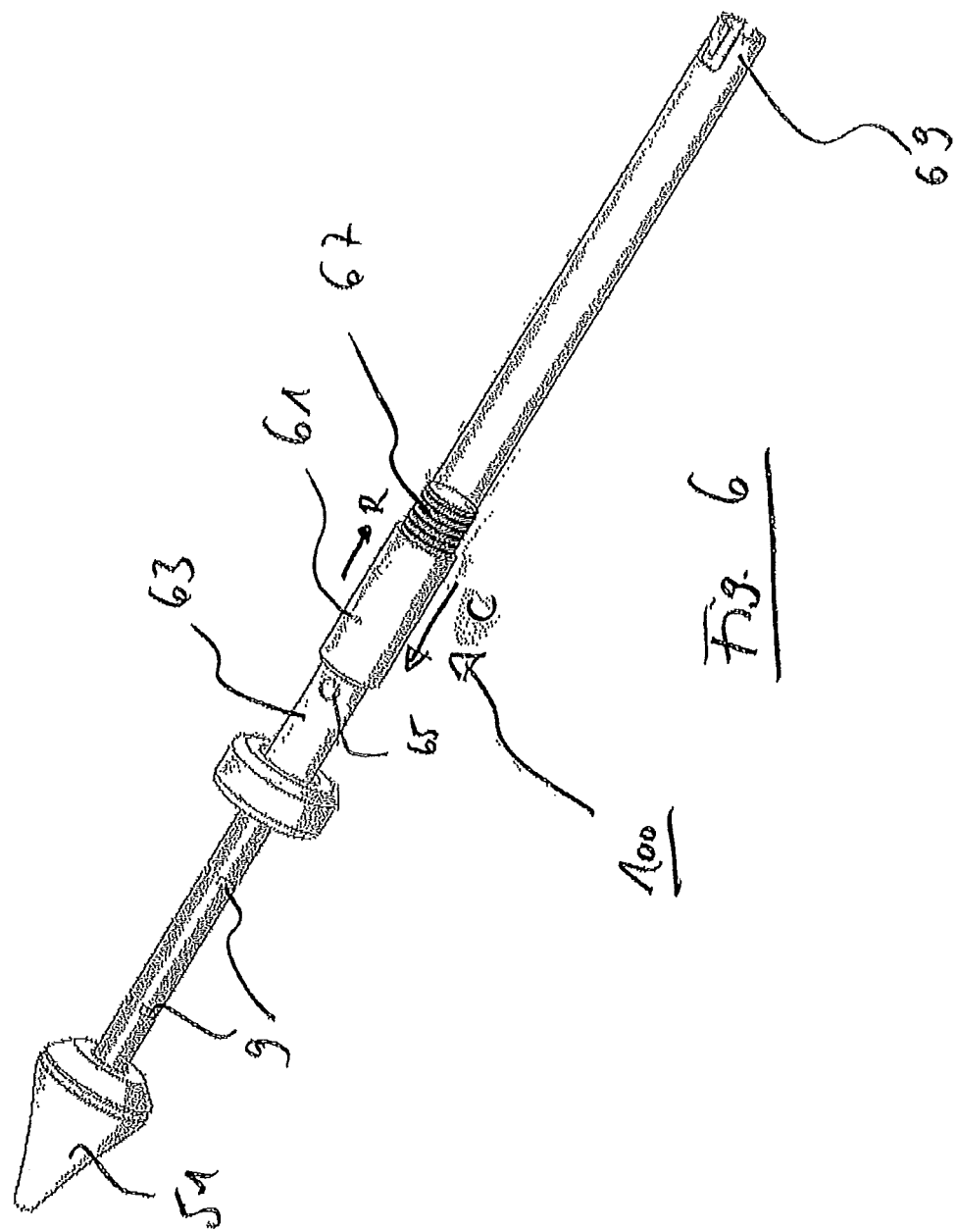
FIG. 6 shows a longitudinal part section through a schematically simplified cutaway view of the apparatus according to the present invention.

FIG. 5 shows the tip 51 of the apparatus 100 of FIG. 4 without the implant 300. In FIG. 6, the wall apertures or shaft apertures 9 through which the threads 11 and 11'—which are also not shown in FIG. 5—exit and enter shaft 1.

Shaft 1 features an arbitrary number of apertures 9, at one, two (as shown in FIG. 5) or more longitudinal heights of the axis.

The shaft apertures 9 extend through the entire thickness of the wall of shaft 1 and, hence, interconnect the lumen or inner space of shaft 1 with the exterior of shaft 1.

The shaft apertures 9 may be evenly spaced from each other around the circumference of shaft 1. Alternatively, they may be divided with at least two different distances from each other around the circumference.

FIG. 6 shows an apparatus 100 according to another exemplary embodiment of the present invention. FIG. 6 does not show an implant. It does not show threads and neither a section thereof to be clamped.

In FIG. 6 a first clamping section 61 and a second clamping section 63 are shown. In the example of FIG. 6, the first and the second clamping sections 61, 63 are both arranged as tube sections. Also by way of example, in FIG. 6 the first and the second clamping sections 61, 63 are arranged with respect to each other in a coaxial manner. Further, in the exemplary embodiment of FIG. 6, the first clamping section 61 which is arranged around the second clamping section 63 may be slid or moved along and relative to the second clamping section 63.

For example, the first clamping section 61 may be slid or moved towards the tip 51 into a clamping position in a direction indicated by the arrow C (for clamping). In this position, the section of the not shown thread would be clamped between the first and the second clamping section. In this particular and exemplary embodiment, the second clamping section 63 may be slid away from the tip 51 into a release position in a direction indicated by the arrow R (for releasing). In this position, the section of the not shown thread would not be clamped any longer between the first and the second clamping section. In the particular exemplary embodiment of FIG. 5, the first clamping section 61 is in any case moved parallel to the longitudinal extension or the main extension of the shaft 1.

As discussed above, in FIG. 6 the apparatus 100 is shown in a release position or state. Also, the section of the threads 11 and 11' to be clamped is not shown in FIG. 6. However, as is readily been understood by one skilled in the art, a section of threads 11, 11', for example the end section thereof, may be clamped between the first and the second clamping sections 61, 63. This is easily accomplished by moving the second clamping section 61 towards the tip 51 into the clamping position not shown in FIG. 6. The section in question may than be clamped between the first clamping section 61 (for example, the inner surface thereof) and the second clamping section 63 (for example, the outer surface thereof).

In FIG. 6, the second clamping section 63 comprises one or more clamping holes 65 through which the section of the threads 11 and 11' to be clamped may be guided from inside of shaft 1 (that is, from its lumen) to the outer surface of the second clamping section 63 and in between the first and the second clamping sections 61, 63.

By way of example, for the ease of moving the first clamping section 61 into the release position shown in FIG. 6 during surgery, the first clamping section 61 may be provided with a thread 67 or any other coupling for interconnecting the first clamping section 61 with a retracting device, or release device, for pulling or retracting the first clamping section 61 in the direction indicated by arrow R. In other exemplary embodiments according to the present invention, the first clamping section 61 is integral with a releasing device.

It goes without saying that everything that has been stated herein for the first clamping section 61 may in further exemplary embodiments according to the present invention which are not shown in the figures also hold true for the second clamping section 63, and vice versa. For example, it may be the second clamping device 63 that is retractable or movable (in whatsoever direction) with regard to the first clamping device 61, in contrast to what is depicted in FIG. 6.

In the example of FIG. 6, the shaft 1 comprises a bayonet coupling 69 for connecting the shaft 1 with further parts of the apparatus. However, many other couplings such as screw threads may do as well and are, therefore, also encompassed by the present invention.

Further, the shaft 1, the first clamping section 61 or any other part of the apparatus 100 and the retracting device, or release device interconnected with the first clamping section 61 by the thread 67 (shown in FIG. 6) or any other coupling may be provided with a click-release lock or the like in order to avoid an unintended release of the first clamping section 61 from the clamping position.

Furthermore, the shaft 1 may have a further groove, sliding block guiding, slotted guide or the like to avoid twisting or rotation of retracting device, or release device with regard to the shaft.

Figure 7:
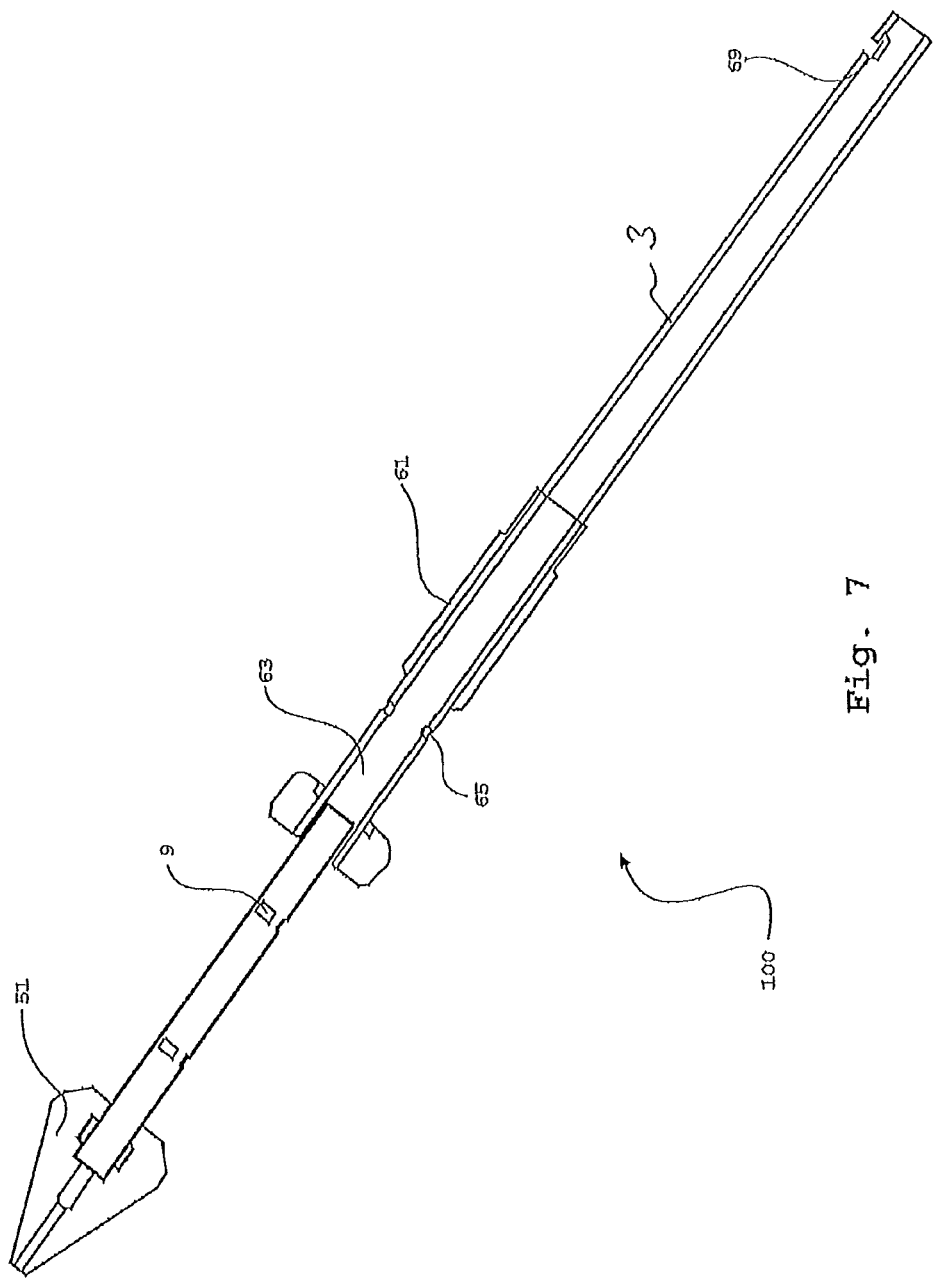
FIG. 7 shows the apparatus of FIG. 6 in a longitudinal section.

FIG. 7 shows the apparatus 100 of FIG. 6 in a longitudinal section.

Figure 8:
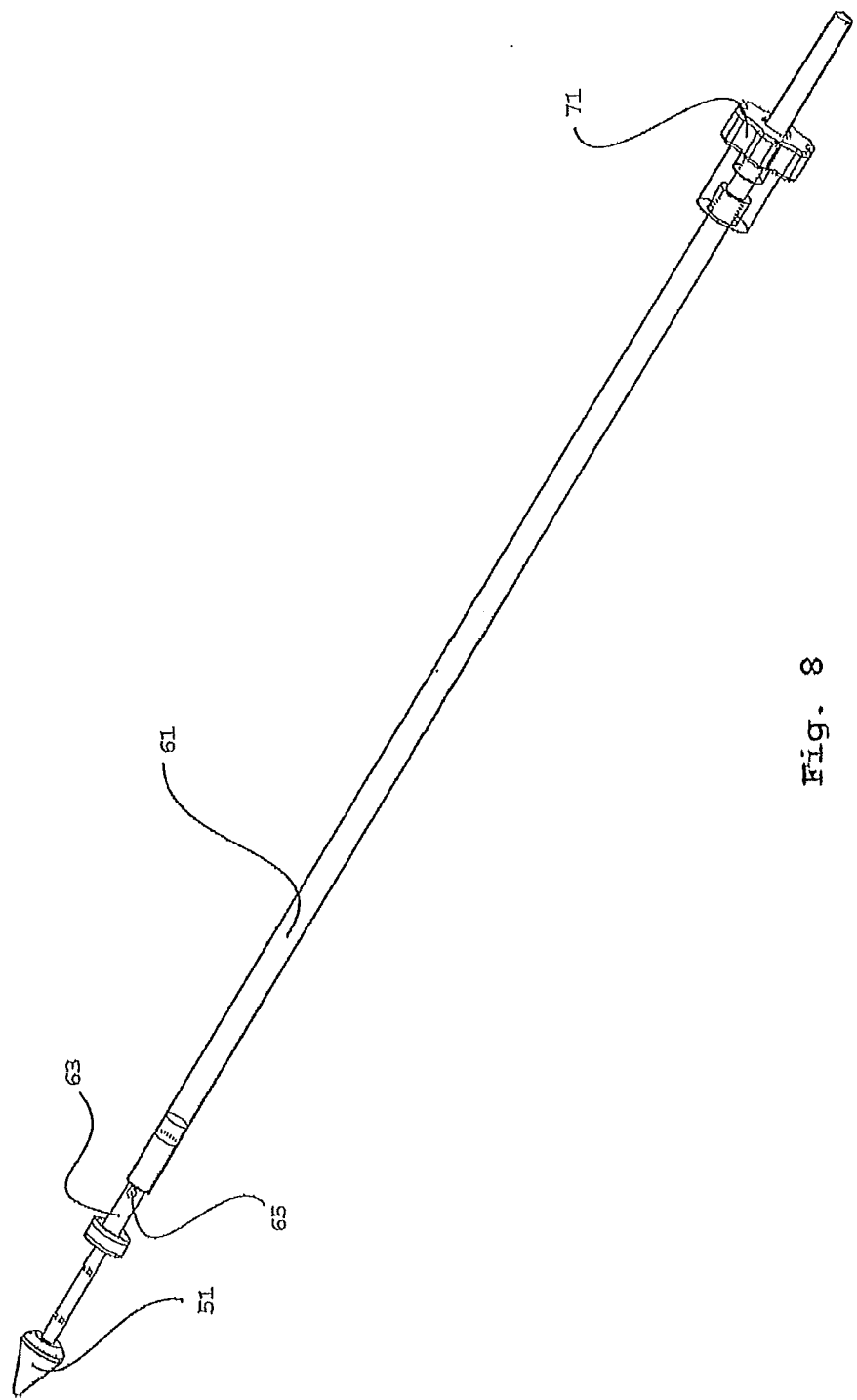
FIG. 8 shows the apparatus according to a further exemplary embodiment of the present invention.

FIG. 8 shows the apparatus 100 according to a further exemplary embodiment of the present invention down to its handle 71 of the of the releasing device. In FIG. 8, the releasing device is integral with the first clamping device 61. It may be retracted by pulling the handle 71.

In FIG. 8, the apparatus 100 is shown in the release or open position or state in which no clamping can occur. However, no implant and no threads are shown.

Figure 9:
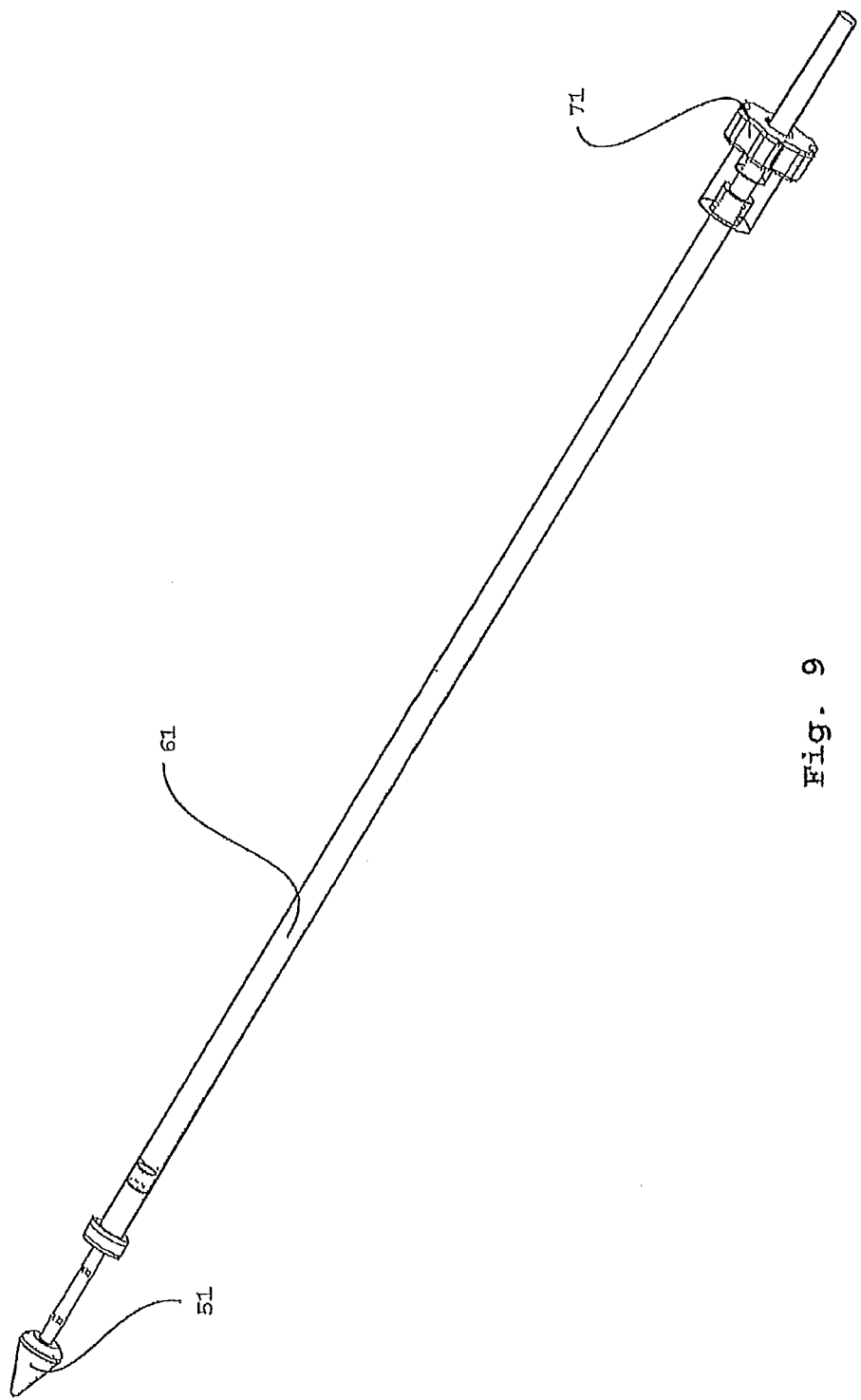
FIG. 9 shows the apparatus of FIG. 8 in a clamping position or state.

FIG. 9 shows the apparatus 100 of FIG. 8. In FIG. 8, the apparatus 100 is shown in the clamping position or state.

Figure 10:
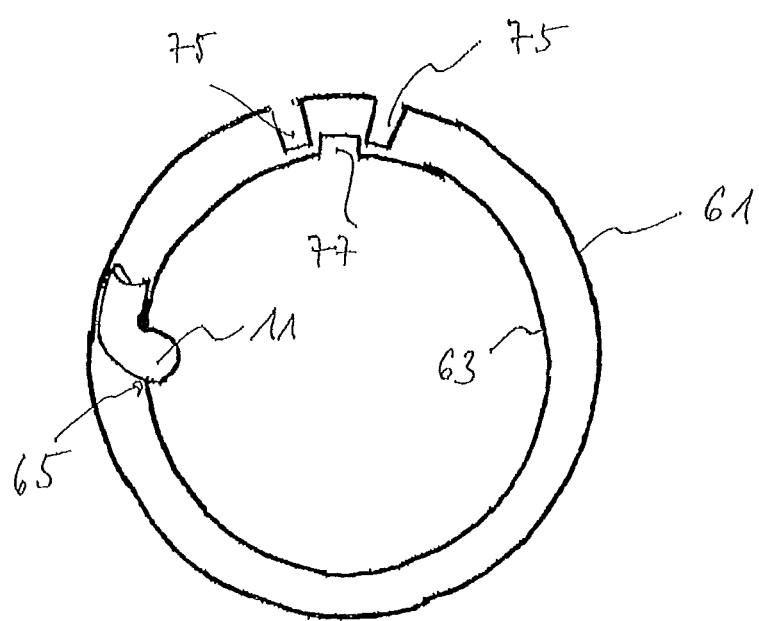
FIG. 10 shows a schematically simplified cross section through the first and the second clamping sections of an exemplary apparatus according to the present invention.

FIG. 10 shows a schematically simplified cross section through the first and the second clamping sections 61, 63 of a first embodiment thereof.

The first clamping section 61 comprises two indentations 75 which together form a groove in which a bulge 77 may be moved in a direction perpendicular to the plane of projection of FIG. 10. The indentations 75 and the bulge 77 disallow, however, a rotation of the first and the second clamping sections 61, 63 relative to each other. That way, the indentations 75 and the bulge 77 act as a mechanism for disabling or for limiting rotation between the first and the second clamping sections 61, 63. Of course, the mechanism for disabling rotation may be embodied in any other suitable manner as well. It may comprise or exist of extensions, indentations, furcations, notches, oval cross sections of one or both clamping sections 61, 63, and so on. The invention is not limited to the exemplary embodiment shown in FIG. 10.

Figure 11:
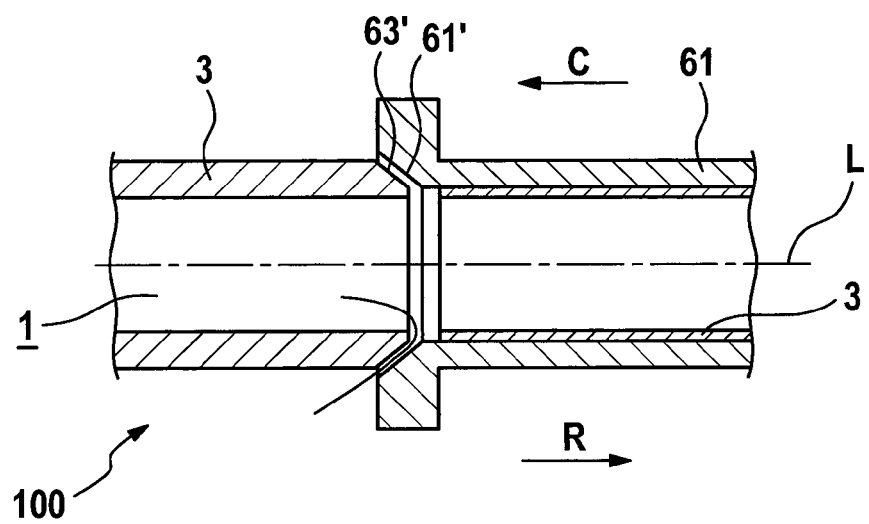
FIG. 11 shows an apparatus according to the present invention in another embodiment, longitudinal cut, in section, revealing the first and the second clamping sections of that embodiment.

FIG. 11 is a cut view of an apparatus 100 according to the present invention in another embodiment in which the first clamping section 61 and the second clamping section 63 of the apparatus 100 are arranged such that they (or respective surfaces or planes thereof) are inclined to the longitudinal axis L of the apparatus 100, its shaft 1, and/or the reception or retaining area 55 for receiving the implant.

In the exemplary embodiment of FIG. 11, the first and the second clamping sections 61, 63 are inclined under the same angle. This way, upon moving the first clamping section 61 along array C (C for "clamping"), an inclined surface 61' is eventually contacted or abutted by an inclined surface 63' of the second clamping section 63 or of wall 3. This way, the clamping may advantageously take place along a longer distance than, e.g., the width of the shaft wall would allow.

The inclined surface 63' of the second clamping section 61' may be part of a collar 79 of the second clamping section 61'.

In the particular embodiment of FIG. 11, arrow C points towards the tip of the apparatus 100.

Figure 12:
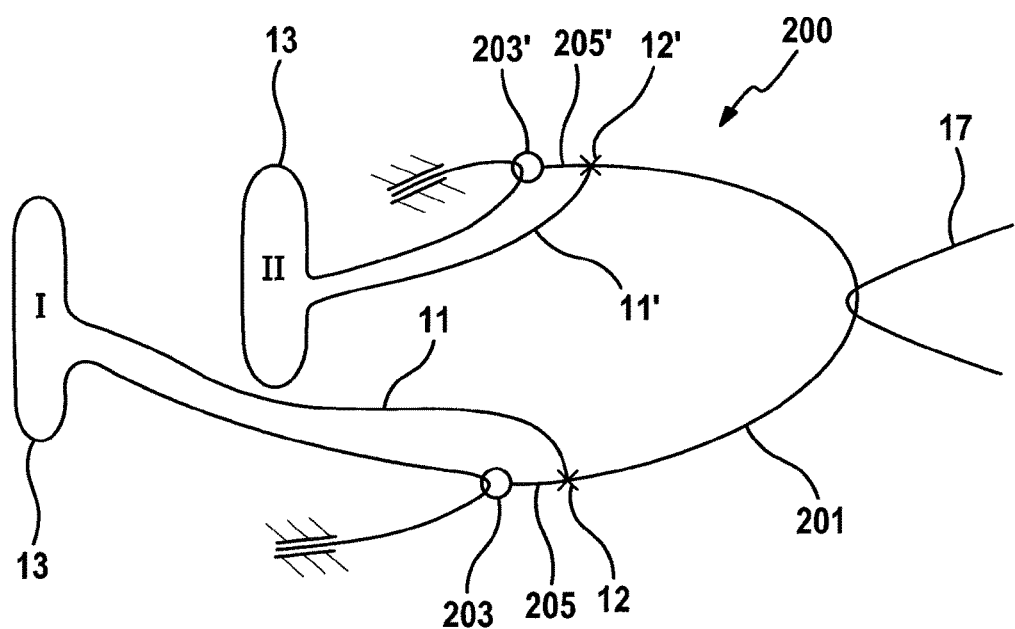
FIG. 12 shows a set according to the present invention in a first embodiment thereof.

FIG. 12 shows a set 200 of tension threads, according to the present invention.

The set 200 of tension threads comprises in the exemplary embodiment of FIG. 12 one first string 201. The first string 201 is connected to the first tension thread 11 and to the second tension thread 11'.

The first string 201 comprises a first guiding element 203 for guiding through the first tension thread 211 and a second guiding element 203' for guiding through the second tension thread 211'. Both the first tension thread 211 and the second tension thread 211' are attached to the first string 201.

In the exemplary embodiment of FIG. 12, both the first tension thread 11 and the second tension thread 11' are attached to the first string 201 by their respective first end sections 12 and 12'. They are attached such that their first end sections are fixed to the first string 201 such that upon withdrawing the first string 201 from the lumen of the apparatus 100 to an outside thereof, the first and second end sections have to follow the first string 201 to the outside once the first and second tension threads 11, 11' are not clamped any more.

For example, the first tension thread and/or the second tension 11, 11' thread may be knotted to or integral with the first string 201.

Both the first and the second tension thread 11, 11' are folded into loops 13 and 13'. By these loops 13, 13' the threads 11, 11' may be inserted into the guiding structures 303 and 303' (not shown in FIG. 12) and hence, wound around the whole circumference of the implant or parts thereof. The implant 300 may, hence, be hold by the threads inside the space I and II.

In the exemplary embodiment of FIG. 12, both the first and the second guiding element 203, 203' are rings. However, any other shape that allows the first and second tension threads 11, 11' to slide forth and back through it (which is a precondition for folding and unfolding the implant 300 not shown in FIG. 12) are suitable and, hence, encompassed by the present invention as well.

As can be seen in FIG. 12, in certain embodiments according to the present invention neither of the first tension thread 11 nor the second tension thread 11' is directly connected to the pulling thread, the tensioning device of a catheter (not shown in the figures) or any other apparatus for altering the shape of the foldable and/or unfoldable implant. Rather, they are in direct contact with the first string 201. It is via the first string 201 that they are in indirect contact with the pulling thread 17 and, hence, the tensioning device as well.

As can be further seen in FIG. 12, in some embodiments according to the present invention the first tension thread 11 is connected to the first string 201 at a first end section 205 of the first string 201. Likewise, by way of example only, the second tension thread 11' is connected to the first string 201 at a second end section 205' of the first string 201. As in FIG. 12, the first end section 205 and the second end section 205' may be opposed ends of the first string 201.

Finally, as can also be seen in FIG. 12, in certain embodiments according to the present invention the first tension thread 11 is connected with its first end section 12 to the first string 201, and/or the second tension thread 11' is connected with its first end section 12' to the first string 201.

FIG. 13 shows another embodiment according to the present invention in which the first string 201 is connected to at least six tension threads 11, 14, 15, 11', 14', 15'. Three of them (11, 14 and 15) are guided through the first guiding element 203. Three of them (11', 14' and 15') are guided through the second guiding element 203'.

As can be seen, all free ends of the six tension threads 11, 14, 15, 11', 14', 15' (i.e., those ends which are not fixedly connected with the first string 201) are clamped by the common first and second clamping sections 61, 63. However, some of the tension threads may as well be clamped by a first clamping mechanism that is different from a second clamping mechanism as this is shown, e.g., in FIG. 12. Of course, more than two clamping sites may as well be contemplated. In fact, each tension thread might even be clamped by one clamping mechanism (as described herein or in a different design) for itself. Providing a sufficient number of clamping mechanisms is subject-matter of certain embodiment according to the present invention.

FIG. 14a shows an longitudinally cut tip of an apparatus 100 according to the present invention in yet another embodiment. It is shown in an unclamping state revealing the first and the second clamping sections 61, 63 of that embodiment.

FIG. 14b shows the tip of the apparatus of FIG. 14b, slightly rotated, but not cut.

As can be seen in FIGS. 14a and 14b, the first clamping section 61 is connected to the tip of the apparatus 100 by a thread such that the first clamping section 61 can be moved along the shaft or wall 3 of the tip by rotating it. The first clamping section 61 can only slide up and down but is not rotatable.

For moving the first clamping section 61 along the longitudinal axis, a first connecting device 81 is provided. The first connecting device 81 may have a crown-shaped end, it may comprise a gear pattern, it may have teeth or any other engagement device, due to space constraints preferably at its front surface (not on its sided surface), configured to be engageable with a second, rotably arranged connecting device (not shown) of the apparatus 100 (not of the tip) in a manner such that via rotating the second connecting device the first connecting device 81 may be rotated.

The first connecting device 81 comprises threads on an outer surface thereof. Also, there are matching threads on an inner surface of the first clamping section 61.

Any rotation of the first clamping section 61 is precluded or avoided by a longitudinal, straight slot provided in a (preferably inner) side or on a circumferential surface of the first clamping section 61 (e. g. by cutting) and a protrusion such as a pin that is arranged within this slot: the first clamping section 61 can only pass by the pin while the pin is guided inside the slot. That way, the first clamping section 61 can be moved to or away from the second clamping section 63 simply by rotating the first connecting device 81. The last named element may be considered as a rotational clamping mechanism. By the rotational clamping mechanism, the clamping surfaces do not rotate in relation to each other. The advantage that comes along with this is that the tension threads to be clamped do neither become damaged nor displaced because of any rotation of the clamping surfaces.

Instead of the slot, a groove might also be provided.

Also, the protrusion such as the pin might as well be a recession whereas the instead of the slot a protrusion might be arrange. In other words, it does not matter whether the first clamping section 61 comprises the slot and the wall 3 comprises the pin, or the other way round.

In the particular exemplary embodiment of FIG. 14a, the pin may be welded onto the inner main tube that can be seen in FIGS. 14a-c, or the wall 3 thereof. The first clamping section 61 is a (preferably short) tube with outer threads and a (preferably) straight slot cut along its length. The first clamping device 61 slides over the wall 3 and its slot is aligned with the pin which in turn is fixed to the wall 3. It is the pin and the slot acting like a crank or a compulsory guiding that prevents the first clamping section 61 from rotating.

The first connecting device 81 comprising the crown is a tube with inner threads that engages the outer threads of 61. When the first connecting device 81 is rotated, it remains at its place with regard to the longitudinal axis of the tip. Its distance to the second clamping section 63 does never change. It does not move in translation. Only, because of the threads the first clamping section 61 is moved towards the clamping hole 65 or away from it. The first connecting device 81 is arranged on an outside of the first clamping section 61, whereas the first clamping section 61 is arranged on an outside of the wall 3.

In other words, the tip of the apparatus 100 comprises a rotational clamping mechanism while the clamping surface as such are arranged so as not to be rotated.

In FIGS. 14a and 14b, the first and the second clamping sections are moved apart from each other such that they would not clamp any tension thread between them (if provided). The clamping hole 65 is open, i. e., not covered by the first clamping section 61.

As can be seen in FIG. 14a, the clamping surface of at least one of the first and second clamping sections 61, 63 is inclined against a longitudinal axis of the apparatus 100 or the tip thereof shown in FIGS. 14a, 14b. The inclination may be between 10 and 30 degree, preferably between 10 and 20 degree, most preferably about 15 degree, since the latter value has been proven to ensure the best clamping effect.

As can be seen in FIGS. 14a, 14b, the entire clamping mechanism is arranged on the tip shown in these figures. Hence, both the first and the second clamping sections 61, 63 are arranged on the tip which is, in some embodiments, detachable from the remaining parts of the apparatus/implant delivery device. The first connecting device 81 may be embodied (as, e. g., in FIG. 14a) such that it has not to be actively connected with the main parts of the apparatus upon assembling tip and apparatus. Rather, there are a number of designs such as the one shown in FIG. 14a that allows that the first connecting device 81 is automatically being connected to the second connecting device upon putting the tip onto the apparatus. This advantageously safes time and effort. Also, connecting the first and second connecting devices together cannot be forgotten.

FIG. 14c shows the tip of the apparatus of FIGS. 14a and 14b in a clamping state. The first and the second clamping sections 61, 63 have been move towards each other and, thus, into contact with each other. This defines the clamping state. The clamping hole 65 is no longer visible. It is covered by the first clamping section 61.

FIG. 15a shows the tip shown in FIGS. 14a-c in an unclamped state.

FIG. 15b shows the tip of FIG. 15a in another unclamped state. One can now see the thread 83 of the first clamping section 61. In preferred embodiments of the present invention, the slot (not shown in the figures) is arranged within the section of the first clamping section 61 that carries the thread 83.

FIG. 15c shows the tip FIGS. 15a and 15b in a clamped state.

By means of the rotational mechanism any longitudinal actuations by the user in order to unclamp the tension threads can be avoided. This is of advantage because longitudinal operations hampers precise positioning of the device: If one of the clamping sections has to be push or pulled (instead of rotated), a counteracting force on the apparatus or the main catheter is required. That counteracting force may result in that the desired position of the implant will change due to this action. This is avoided by the rotational clamping.

REFERENCE NUMERALS 100 apparatus
200 set
201 first string
203 first guiding element of the first string
203' second guiding element of the first string
205 first end section of the first string
205' second end section of the second string
300 implant
303 first guiding structure of the implant
303' second guiding structure of the implant
305 post
307 opening
1 shaft
3 wall of shaft 1
9 apertures
11 first tension thread(s), also 14, 15
11' second tension thread(s), also 14', 15'
12 first end section of first tension thread
12' first end section of second tension thread
13 loop of the first tension thread
13' loop of the second tension thread
17 pulling thread
51 tip
53 external protective sleeve
55 reception/retaining area
57 collar
61 first clamping section
63 second clamping section
65 clamping holes
67 thread
69 bayonet coupling
71 handle of releasing device
75 indentations
77 bulge
79 collar
81 first connecting device
83 thread
L longitudinal direction
C direction of clamping
R direction of release or unclamping
I space for the first guiding structure of the implant
II space for the second guiding structure of the implant

The invention claimed is:

1. An apparatus for folding or unfolding at least one medical implant by using one or more tension threads, wherein the apparatus includes:
   a shaft including a reception or retaining area for receiving the implant;
   a tensioning device for altering a shape of the foldable and/or unfoldable implant by using at least one of the one or more tension threads or by using at least one first string connected to the one or more tension threads; and
   a clamping mechanism configured for engaging and clamping at least one section of at least one of the one or more tension threads.

2. An apparatus according to claim 1, comprising:
   a releasing device for releasing the clamped section of the one or more tension threads from the implant or from the clamping mechanism by releasing the clamping mechanism.

3. An apparatus according to claim 2, wherein the clamping mechanism is adapted for clamping the at least one section of at least one of the one or more tension threads between a first clamping section of the apparatus and a second clamping section of the apparatus, or wherein the clamping mechanism consists of the first and second clamping sections.

4. An apparatus according to claim 1, wherein the clamping mechanism is adapted for clamping the at least one section of at least one of the one or more tension threads between a first clamping section and a second clamping section, or wherein the clamping mechanism consists of the first and second clamping sections.

5. An apparatus according to claim 4, wherein the first clamping section and the second clamping section are arranged such that at least one of them is slidable relatively to the other.

6. An apparatus according to claim 4, wherein the first clamping section and the second clamping section are arranged such that they are inclined relative to the longitudinal axis of the apparatus, the shaft, and/or the reception or retaining area for receiving the implant.

7. An apparatus according to claim 4, wherein the second clamping section is arranged in an inner space of the first clamping section.

8. An apparatus according to claim 4, wherein the first clamping section and the second clamping section are arranged such that at least one of them may slide relatively to the other.

9. An apparatus according to claim 4, wherein the first clamping section and the second clamping section are arranged such that they are inclined relative to the longitudinal axis of the apparatus the shaft, and/or the reception or retaining area for receiving the implant.

10. An apparatus according to claim 4, wherein the second clamping section is arranged in an inner space of the first clamping section.

11. An apparatus according to claim 1, wherein an interior of the shaft is permeable or may be passed in at least sections thereof in the longitudinal direction of the shaft, wherein the shaft has a wall, wherein the shaft includes at least one shaft aperture, through which the one or more tension threads for folding and/or unfolding the implant may enter and/or exit.

12. An apparatus according to claim 1, wherein the implant is a stent or a cardiac valve assembly.

13. An apparatus according to claim 1, wherein the apparatus and the at least one medical implant are connected with the one or more tension threads or with a set of tension threads for folding or unfolding the at least one medical implant.

14. An apparatus according to claim 13, wherein the set of tension threads comprises at least one first string, at least a first tension thread, and at least a second tension thread, wherein
   the first string comprises a first guiding element for guiding through the first tension thread and a second guiding element for guiding through the second tension thread, and wherein
   both the first tension thread and the second tension thread are attached with the first string.

15. An apparatus according to claim 14, wherein at least one of the first guiding element and the second guiding element is a ring.

16. An apparatus according to claim 14, wherein the first string is connected to at least six tension threads, at least three of the at least six tension threads being guided through the first guiding element, and at least three of the at least six tension threads being guided through the second guiding element.

17. An apparatus according to claim 14, wherein the first tension thread is connected to the first string at a first end section of the first string, and the second tension thread is connected to the first string at a second end section of the first string.

18. A medical implant comprising a set of tension threads for folding or unfolding the medical implant or being connected or provided herewith, the set of tension threads being designed as set forth claim 13.

19. An apparatus according to claim 1, wherein the clamping mechanism is configured to release the one or more tension threads such that the one or more tension threads are removable from the at least one medical implant.

20. An apparatus according to claim 1, wherein the clamping mechanism includes a first clamping surface and a second clamping surface, the at least one section of at least one of the one or more tension threads being sandwiched between the first clamping surface and the second clamping surface.

21. A set of tension threads for folding or unfolding at least one medical implant, the set of tension threads comprising:
   at least one first string, at least a first tension thread and at least a second tension thread, wherein
   the first string comprises at least a first guiding element for guiding through the first tension thread and a second guiding element for guiding through the second tension thread, the first guiding element being configured to be moveable relative to the second guiding element and wherein
   both the first tension thread and the second tension thread are attached with the first string.

* * * * *